United States Patent [19]

Roller

[11] 4,443,492

[45] Apr. 17, 1984

[54] RATE OF ABSORBENCY OF SUBSTRATES CONTAINING IN-SITU POLYMERIZED MONOMERS

[75] Inventor: Judy Roller, North Brunswick, N.J.

[73] Assignee: Personal Products Company, Milltown, N.J.

[21] Appl. No.: 485,783

[22] Filed: Apr. 18, 1983

[51] Int. Cl.$^3$ ............................................. B05D 3/06
[52] U.S. Cl. ................................ 427/44; 204/159.14; 204/159.22; 427/331; 427/336; 428/290; 604/367; 604/372; 604/378
[58] Field of Search .......................... 427/44, 331, 336; 428/290; 604/367, 372, 378; 204/159.22, 159.14

[56] References Cited

U.S. PATENT DOCUMENTS

| | | | |
|---|---|---|---|
| 3,901,236 | 8/1975 | Assarsson | 604/372 |
| 3,950,574 | 4/1976 | Butler | 427/336 |
| 4,008,353 | 2/1977 | Gross et al. | 428/290 |
| 4,143,218 | 3/1979 | Adams et al. | 427/336 |
| 4,192,727 | 3/1980 | Ward | 204/159.22 |
| 4,232,674 | 11/1980 | Melican | 604/372 |
| 4,340,057 | 7/1982 | Bloch et al. | 604/372 |

Primary Examiner—John H. Newsome
Attorney, Agent, or Firm—Jason Lipow

[57] ABSTRACT

An improvement in a process for producing an absorbent composite wherein a solution of acrylic or methacrylic acid salts are applied to a substrate and irradiated to form a water swellable polymer in-situ within such substrate. The component comprises saturating the irradiated substrate with an aqueous liquid and then drying to a moisture content of less than 20 percent by weight whereby the dried substrate exhibits rapid absorption properties.

6 Claims, No Drawings

RATE OF ABSORBENCY OF SUBSTRATES CONTAINING IN-SITU POLYMERIZED MONOMERS

BACKGROUND OF THE INVENTION

This invention relates to absorbent materials and in particular to absorbent materials wherein a formed fibrous substrate has deposited thereon a solution or dispersion of monomers and then is subjected to irradiation whereby said monomers polymerize in-situ, within the matrix of the fibers of the substrate. The resulting polymers are highly hydrophillic and greatly add to the absorbancy of the substrates.

Such absorbent materials may be employed in a wide variety of products and, in particular, in products for absorbing body fluids such as diapers, wound dressings, sanitary napkins, tampons, incontinent pads and the like. A method of making such absorbent materials is described in co-pending U.S. patent application Ser. No. 149,215, filed on May 12, 1980 by P. H. Ericksen, et al.

While each of these prior suggestions have produced a highly absorbent material well suited for use in the products being considered herein, the material still suffers, to a degree, from drawbacks inherent in the use of highly hydrophillic polymers. Specifically, it has been found that when such polymers become wet with fluid there is a tendency to form an occlusive film over the surface of the polymer particle, thereby precluding or at least greatly inhibiting, further penetration of liquid into the interior of the particle. The result is that while these polymers ultimately exhibit a high maximum capacity to absorb liquids, it takes a substantial time interval to reach this high capacity.

The art is now replete with suggestions for reducing this time interval including for example widely dispersing the polymers throughout a matrix of rapidly wicking material e.g., cellulose fiber webs, and controlling the particle size of the polymers. Most recently, in the above described patent application and patent, in-situ polymerization has been suggested for improving the distribution of hydrophillic polymers within an absorbent web and thereby decrease the time interval to attain maximum capacity.

While, in the main, each of the prior suggestions have in fact reduced the time interval for attaining maximum capacity, it is still highly desirable that further reduction be attained.

SUMMARY OF THE INVENTION

In accordance with the teachings of this invention an improvement has been made in a process for depositing monomer onto a formed fibrous web and irradiating the web to polymerize the monomer in situ. Specifically, the improved process results in a marked decrease in the time interval required to reach maximum absorption capacity.

The improvement is provided in a process for producing an absorbent composite wherein a formed, fibrous substrate has applied thereto, an aqueous metal salt of acrylic or methacrylic acid. The substrate containing the monomer solution is then irradiated with sufficient electromagnetic or corpuscular ionizing radiation to convert said salt of acrylic or methacrylic acid to a water swellable polymer.

In accordance with this invention, it has been discovered that the above process is improved when the now irradiated substrate is saturated with water and then dried to a moisture content of less than about 20 percent by weight. Preferably, the substrate is dried to a moisture content of less than 15 percent e.g., 10 percent by weight.

By the addition of these relatively simple saturating and drying steps it has been discovered that the time interval required for the final composite to reach its maximum capacity has been decreased by factors of 20 or more, with concomitant decreases in the time required to approach various degrees of maximum capacity.

DETAILED DESCRIPTION OF THE INVENTION

The invention comprises the steps of depositing a solution of monomer onto a formed fibrous web, irradiating the deposited web with electromagnetic or corpuscular ionizing radiation to polymerize the monomer; saturating the web with liquid and then drying the saturated web to a liquid content of less than 20 percent by weight.

An aqueous solution of a salt comprising fully or partially neutralized acrylic or methacrylic acid is employed in the invention. The salt employed can be an ammonium salt or an alkali metal salt such as a sodium or potassium salt. The degree of neutralization employed can vary in particular cases, in view of several factors. For instance, at the preferred high solution concentrations, sodium acrylate may begin to precipitate when the degree of neutralization begins to exceed about 85 percent. Therefore, it is preferred to employ sodium acrylate at about a 60 to 85 percent degree of neutralization. The more soluble ammonium and potassium acrylates, or mixed salt acrylates, can be employed at higher degrees of neutralization.

Pure methacrylate polymers do not cross-link under radiation. Therefore, methacrylate salts are used only in a mixture with acrylic salts or with a water-soluble cross-linking monomer, as explained below.

The preferred aqueous solution for use in the invention comprises an aqueous solution of sodium acrylate.

It is permissible to include other materials in the aqueous solution. Such materials include polyfunctional, ethylenically unsaturated compounds such as methylene-bis-acrylamide, and polyethylene glycol diacrylates or dimethacrylates such as tetraethylene glycol diacrylate. These materials are employed as cross-linking agents. The polyfunctional monomer is used in small amounts, for instance, in amounts of less than one mol percent, based on moles of acrylate salts(s).

A water-soluble polymer can be employed as a viscosity adjusting agent, for example, to improve the printing characteristics of the salt solution. Examples include polyvinyl pyrrolidone, hydroxyethyl cellulose, and similar materials. Colloidal silica, a thixotropic agent, can be employed for the same purpose.

Finely divided fillers may also be employed as extenders. Examples include talc, clay, diatomaceous earth, perlite, and the like.

Small amounts of polyvalent metal ions may be added to the salt to provide ionic cross-linking. Illustrations include calcium, magnesium, and aluminum.

The aqueous solution is applied in a predetermined pattern onto a formed fibrous substrate. The fibrous substrate can be a loosely formed batt of fibers, a carded or an air-layed web, tissue paper, a woven fabric such as cotton gauze, a knitted fabric, or a nonwoven fabric. By "formed" fibrous substrate is meant that the fibrous substrate need not undergo any further web-forming operation in order to be employed in an article, although it may require cutting, bonding, shaping, etc., in order to be fabricated into an article. It is generally preferred to employ absorbent fibers in the fibrous substrate such as cellulosic fibers including wood pulp, rayon, and cotton. It is permissible, however, to include other types of fibers in the formed fibrous substrate.

The aqueous solution is applied to the formed fibrous substrate in a predetermined pattern. It is preferred to employ an intermittent pattern such as an intermittent pattern of fine dots, intermittent stripes, or the like. The pattern can be employed to produce "dams", "wicking channels", or the like, in the absorbent composite that is produced by the process of the invention. For instance, a diaper having a continuous strip of cross-linked absorbent polymer around the edges of the absorbent padding portion of the diaper will have less tendency to leak around the edges. In general, it is preferred to employ a pattern of very finely divided discrete areas in order to provide as high a ratio of polymer surface area to mass as possible. The reason for this is to utilize the absorbent capacity of the polymer to the fullest extent possible.

The aqueous solution can be applied to the fibrous substrate in the predetermined pattern by means such as printing, spraying, flowing through nozzles, kiss coating, saturating, or the like.

If desired, the aqueous solution can be applied to the fibrous substrate in an overall pattern, which may be applied in an amount sufficient to simply coat one surface of the fibrous substrate or it can be employed in a quantity sufficient to penetrate as much of the thickness of the fibrous substrate as is desired in particular cases.

The amount of aqueous solution added to the fibrous substrate is not narrowly critical, and can vary over a rather wide range, depending on factors such as end-use application for the product, and similar considerations. Thus, the add-on (on a solids basis) can vary from less than 1 percent up to several hundred percent, based on weight of fibrous substrate.

After the aqueous solution has been applied to the fibrous substrate, the material is then irradiated by electromagnetic or corpuscular ionizing radiation such as accelerated electrons, gamma rays, or the like, sufficient to convert the acrylic and/or methacrylic salt to a water-swellable polymer. The dose employed in particular cases will vary somewhat, depending on factors such as presence or absence of cross-linking monomers, desired degree of polymerization of the polymer, degree of cross-linking desired, and the like. In general, it is desired to irradiate the first composite with doses in excess of about two megarads, and preferably in excess of about three megarads. Particularly when using lower doses, it may be desirable to purge oxygen from the aqueous salt solution (as by bubbling nitrogen through the solution). The maximum dose would be that dose at which degradation of the substrate begins. With cellulosic substrates, the literature reports that the dose at which degradation begins is about six megarads when gamma radiation is employed. Other forms of radiation would be expected to cause degradation at about the same dose.

In accordance with the teachings herein, after irradiating, the fibrous substrate is next saturated with an aqueous liquid and preferably with water. This may be accomplished by simply submerging the irradiated substrate in a vessel of such liquid, by padding or spraying liquid onto the substrate or by any other means which will achieve saturation. In order to insure saturation, the liquid should be available in great excess. Generally, saturation can be observed by eye in that, at the points on the substrate where irradiated monomer exists, the substrate will swell and continue to do so until saturated. By simple experiment, the residence time and excess water requirement may be determined for given process conditions.

The saturated substrate is next dried to a moisture content of less than 20 percent, by weight, and preferred less than 15 percent by weight. Drying may be accomplished by various methods known in the art, including, without limitation, steam cans, forced air ovens, infrared lamps or the like.

The resulting substrate, having undergone the steps of saturation and drying, exhibits an extremely short time interval requirement to reach maximum absorption capacity, as defined hereinafter, when contrasted with substrates which have been merely irradiated and dried. Without being bound to any theory, it is believed that such improvement is the result of modifying the morphology of the in-situ polymerized polymer by virtue of the swelling action upon saturation and the removable of water therefrom.

To illustrate the advantages of the invention, the following example is given:

EXAMPLE

A formed fibrous substrate comprising a web of soft and lofty, through-bonded nonwoven fabric weighing about 3 ounces per square yard is employed. The fabric contains about 25 weight percent rayon staple fibers and about 75 percent wood pulp fibers. The fabric is more particularly described by Liloia, et al. in U.S. Pat. No. 3,663,238.

An aqueous solution is applied in broad stripes to the surface of the fabric. The solution comprises 85 percent neutralized sodium acrylate and is prepared by mixing 50 percent aqueous acrylic acid solution with 50 percent aqueous hydroxide solution to a pH of about 6. The resulting solution contains about 57 percent water. Nitrogen gas is bubbled through the dispersion to purge it of oxygen. The add on level (solid basis) in the area of application is about 460 percent. All percentages described herein are by weight.

The web is passed to a station where it is irradiated with accelerated electrons. The electron beam apparatus is a Dynamitron accelerator capable of providing a voltage of 80 kv. The web is irradiated with a dose of 4 megarads. A portion of the irradiated web is dried over a set of drying cans and used as the "untreated sample". A second portion of the web is submerged in a water bath until no further visible swelling is noted. This portion is next dried, by air drying overnight, to an approximate moisture content of 10 percent by weight and is used as the "treated sample".

Both the treated and untreated samples are tested to determine their rate of absorption. The method employed is to utilize the Porous Plate Testing apparatus, as described in detail in Textile Res. J. 37 pp. 356–366, 1967. Briefly, this involves placing a sample to be tested in what is essentially a Buchner Funnel having a porous bottom plate and holding the sample in place by applying thereon a standard weight to maintain a standardized continuing pressure. The porous plate is placed in contact with a reservoir of liquid and the sample is allowed to absorb liquid through the porous plate until saturated. By maintaining the sample at essentially the level of the reservoir, the fluid absorbed is subjected to essentially zero hydraulic level with respect to the reservoir.

An approximate 0.63 g disc of both the treated and untreated samples were tested on this apparatus and the elapsed time from the start of absorption to equilibrum is recorded as a function of the volume of liquid absorbed. The test liquid is a one percent by weight NaCl aqueous solution and the confining pressure is 0.07 psig. Table 1 below set out the results:

TABLE 1

| Porous Plate Absorbency | | | |
|---|---|---|---|
| Treated Sample | | Untreated Sample | |
| Time (min.) | Amount of 1% Saline Absorbed (ml.) | Time (min.) | Amount of 1% Saline Absorbed (ml.) |
| 1.50 | 0.5 | 0.50 | 0.50 |
| 2.67 | 1.0 | 0.80 | 1.00 |
| 3.90 | 1.5 | 1.35 | 1.50 |
| 4.99 | 2.0 | 2.67 | 2.00 |
| 6.04 | 2.5 | 9.00 | 2.50 |
| 7.09 | 3.0 | 15.00 | 2.76 |
| 8.15 | 3.5 | 45.00 | 3.30 |
| 9.42 | 4.0 | 80.00 | 3.60 |
| 11.66 | 4.5 | 90.00 | 3.67 |
| 17.62 | 5.0 | 105.00 | 3.76 |
| 36.95 | 5.5 | 120.00 | 3.84 |
| 60.00 | 5.8 | 160.00 | 4.02 |
| 75.00 | 5.9 | 180.00 | 4.12 |
| 90.00 | 6.0 | 270.00 | 4.46 |
| 105.00 | 6.0 | 1241.00 (20.7 hrs) | 6.06 |
| 120.00 | 6.1 | 1280.00 | 6.06 |
| 135.00 | 6.1 | | |

TABLE 1-continued

As is indicated in Table 1, the time to reach essentially the same equilibrum value of about 6.1 ml of absorbed fluid was 120 minutes for the treated sample as compared to 1241 minutes for the untreated sample. Simultaneously, prior to attaining equilibrium, the treated sample required 11.66 minutes to absorb 4.5 ml of liquid whereas the untreated sample reached the same degree of saturation only after an elapsed time of 270 minutes.

What is claimed is:

1. In a process for producing an absorbent composite wherein a formed fibrous substrate has applied thereto an aqueous solution comprising an ammonium or alkali metal salt of acrylic or methacrylic acid and is then irradiated with sufficient electromagnetic or corpuscular ionizing radiation to convert said salt of acrylic or methacrylic acid to a water swellable polymer, the improvement wherein:

said irradiated substrate is saturated with an aqueous liquid and then dried to a moisture content of less than 20 percent, by weight whereby said dried substrate exhibits rapid absorption properties.

2. The process of claim 1 wherein said saturated irradiated substrate is dried to a moisture content of less than 15 percent.

3. The process of claim 1 wherein the fibrous substrate is a loose batt of fibers.

4. The process of claim 1 wherein the fibrous substrate is an air layed web.

5. The process of claim 1 wherein the fibrous substrate comprises cellulosic fibers.

6. The absorbent composite produced by the process of claim 1.

* * * * *